(12) United States Patent
Adams et al.

(10) Patent No.: US 9,198,992 B2
(45) Date of Patent: Dec. 1, 2015

(54) STERILE LIQUID TRANSFER PORT

(75) Inventors: Richard H. Adams, Anchorage, AK (US); Miles A. Close, Lino Lakes, MN (US); Amos E. Avery, Kenyon, MN (US)

(73) Assignee: Delaware Capital Formation, Inc., Wilmington, DE (US)

( * ) Notice: Subject to any disclaimer, the term of this patent is extended or adjusted under 35 U.S.C. 154(b) by 1209 days.

(21) Appl. No.: 13/122,222

(22) PCT Filed: Oct. 5, 2009

(86) PCT No.: PCT/US2009/059532
§ 371 (c)(1),
(2), (4) Date: Jul. 6, 2011

(87) PCT Pub. No.: WO2010/040126
PCT Pub. Date: Apr. 8, 2010

(65) Prior Publication Data
US 2011/0256021 A1    Oct. 20, 2011

Related U.S. Application Data

(63) Continuation-in-part of application No. 12/245,603, filed on Oct. 3, 2008, now abandoned.

(51) Int. Cl.
*A61L 2/07* (2006.01)
*A61L 2/26* (2006.01)

(52) U.S. Cl.
CPC ... *A61L 2/26* (2013.01); *A61L 2/07* (2013.01); *Y10T 137/8593* (2015.04)

(58) Field of Classification Search
CPC ............... A61L 2/18; F15D 1/00; B65D 1/00
USPC ............... 422/28, 292; 137/561 R; 220/752
See application file for complete search history.

(56) References Cited

U.S. PATENT DOCUMENTS

| | | | |
|---|---|---|---|
| 4,347,877 A | 9/1982 | Hoiss | |
| 5,460,439 A | 10/1995 | Jennrich et al. | |
| 5,523,519 A | 6/1996 | Weber et al. | |

(Continued)

FOREIGN PATENT DOCUMENTS

| | | |
|---|---|---|
| EP | 0 661 062 A2 | 7/1995 |
| EP | 0661062 | 7/1995 |

(Continued)

OTHER PUBLICATIONS

Central Research Laboratories, "CRL Double Door Sealed Transfer System", www.centres.com/nuclear/ddts.htm Jan. 21, 2006, 1-2.

(Continued)

*Primary Examiner* — Sean E Conley
(74) *Attorney, Agent, or Firm* — Pauly, DeVries, Smith & Deffner

(57) ABSTRACT

A sterilization system for a sterile liquid transfer port system includes an isolation wall having a first and second side, an alpha assembly spanning a port in the isolation wall between the first and second sides of the isolation wall and a beta assembly configured for connection with the alpha assembly from the first side of the isolation wall for sterile transfer of a product. The system further includes a docking cover on the first side of the isolation wall which can mate to the beta assembly during a sterilization process.

7 Claims, 14 Drawing Sheets

(56) References Cited

U.S. PATENT DOCUMENTS

| | | | |
|---|---|---|---|
| 5,562,882 | A | 10/1996 | Smith et al. |
| 5,662,581 | A | 9/1997 | Jennrich et al. |
| 5,732,843 | A | 3/1998 | Glachet et al. |
| 7,044,347 | B1 | 5/2006 | Pedrini |

FOREIGN PATENT DOCUMENTS

| | | |
|---|---|---|
| EP | 0830896 | 3/1998 |
| EP | 0 830 896 A2 | 5/2003 |
| EP | 2379120 | 4/2014 |
| GB | 2237816 | 5/1991 |
| WO | WO 2007/044347 | 4/2007 |
| WO | 2007044347 | 12/2007 |
| WO | WO 2010/040126 | 4/2010 |
| WO | 2010040126 | 9/2010 |

OTHER PUBLICATIONS

Central Research Laboratories, "CRL Double-Door Sealed Transfer System Operating Principle", www.centres.com/nuclear/ddts/ddtsoper, at least as early as Jan. 21, 2006, 1-2.

Central Research Laboratories, "CRL Pharmaceutical Products Catalogue", at least as early as Aug. 20, 2007, 1-18.

Central Research Laboratories, "Steam In Place (SIP) 105mm Alpha & Beta Brochure", at least as early as Aug. 20, 2007, 1-2.

Germfree, "Germfree Containment Without Limitations", www.germfree.com/researchgb.htm, at least as early as Jan. 19, 2006, 1-2.

La Calhene, "DPTE Container Liquid Transfer Brochure", at least as early as Aug. 20, 2007, 1-2.

International Search Report and Written Opinion, International Application No. PCT/US2009/059532, dated Jun. 16, 2010 (17 pages).

"Non-Final Office Action Received", mailed Dec. 23, 2011 in co-pending Application Serial No. 121245,603, "Sterile Liquid Transfer Port," (7 Pages).

"PCT Notification Concerning Transmittal of International Preliminary Report on Patentability", from International Application No. PCT/US2009/059532, corresponding to U.S. Appl. No. 12/245,603, mailed Apr. 14, 2011, pp. 1-10.

Communication Pursuant to Rules 70(2) and 70a(2) EPC and Reference to Rule 39(1) EPC, for European Patent Application No. 14155832.0, mailed Jun. 3, 2014 (2 page).

"Extended European Search Report", for EP Application No. 14155832.0, mailed Apr. 28, 2014 (5 pages).

"Official Action", for Japanese Patent Application No. 2011-530289, mailed Jul. 30, 2013 (10 pages) with English translation.

"Response to Communication Pursuant to Rules 70(2) and 70a(2) EPC", for European Patent Application No. 14155832.0 filed with the EPO Nov. 28, 2014 (16 pages).

"Office Action", for Japanese Patent Application No. 2011-530289, mailed Aug. 29, 2014 (10 Pages) with English translation.

STERILE LIQUID TRANSFER PORT

This application is being filed as a National Stage of PCT International Patent application no. PCT/US2009/059532, entitled "STERILE LIQUID TRANSFER PORT", filed on Oct. 5, 2009, in the name of Delaware Capital Formation Inc., a U.S. national corporation, applicant for the designation of all countries except the U.S., and Richard H. Adams, a U.S. Citizen, Miles A. Close, a U.S. Citizen, and Amos E. Avery, a U.S. Citizen, applicants for the designation of the U.S. only, which is a Continuation in Part of U.S. patent application Ser. No. 12/245,603, filed Oct. 3, 2008; the contents of which are herein incorporated by reference.

FIELD OF TECHNOLOGY

A transfer port apparatus and method enables the uncontaminated transfer of a sterile liquid from a relatively dirty environment to a relatively clean environment through a transfer port in an isolation wall that separates the dirty environment from the clean environment.

SUMMARY

A bulk quantity of sterile liquid product must be transferred to smaller containers for distribution to end users. The transfer process begins by filling a product tank with product. The sterile liquid product is then conveyed from inside the product tank, through the inside of a product hose, and through the inside of a product tube. The product tube is a part of a transfer port apparatus. The sterile liquid is conveyed from the product tube into a filling hose and then into filling equipment, which sequentially fills a number of smaller containers.

Prior to being filled with the sterile liquid product, the interiors of the product tank, product hose, and product tube may be contaminated by biological agents and nonviable particles, such as dust. Both the biological agents and the nonviable particles will compromise the sterility of the sterile liquid product unless they are removed prior to filling the product tank and associated conduits. The sterile liquid transfer port rids the contamination by steam cleaning the product tank and associated conduits by use of a beta assembly and a sterilization docking cover.

Furthermore, the relatively dirty environment can contaminate the cleaner environment with nonviable particles. To avoid contamination of the cleaner environment, in which filling of the smaller containers takes place, a physical barrier between the dirty environment, in which the product tank is located, and the clean environment is interposed. The barrier is comprised of the alpha assembly of the sterile liquid transfer port in conjunction with the beta assembly.

Accordingly, the sterile liquid transfer port ("SLTP") provides for safe, fast, economical, and cost effective (i) sterilization of the product container and conduits through which the sterile liquid product is transferred and (ii) isolation of the less clean environment from the clean environment.

Transfer of liquid product from a sterilized interior of the product tank 202 (located in the product suite 205) to the filling equipment 209 (located in the filling suite 204) is a fairly simple task once sterilization is complete. Transfer of the sterile liquid product is through a transfer port 201*b* in an isolation wall 201.

The alpha assembly of the SLTP also isolates the product suite 205, the less clean environment, from the filling suite 204, the clean environment. The product suite 205 houses a product tank 202 for containment of a bulk quantity of a sterile liquid product. The filling suite 204 houses filling equipment 209 for commercial packaging of smaller amounts of product. Typically, the product suite 205 has a lower level of cleanliness (for example, a Class 10,000 environment) than the filling suite 204 (for example, a Class 100 environment).

An example of the use of the SLTP is a pharmaceutical setting. The pharmaceutical setting gives rise to a requirement for moving a biological agent from the product suite 205 to the filling suite 204, where relatively small quantities of product are transferred into containers for distribution, such as aseptic vials and syringes.

In one embodiment, the SLTP is comprised of an alpha assembly, a beta assembly, and a sterilization docking cover. The transfer port apparatus can also be comprised of (a) an isolation wall; (b) a product suite on a first side of the isolation wall; (c) a filling suite on a second side of the isolation wall; (d) an alpha assembly spanning a port in the isolation wall between the first and second sides of the isolation wall; (e) a product tank; (f) a means for sterilization of the product tank, a conduit, and a beta assembly; (g) the beta assembly configured for connection with the alpha assembly for sterile transfer of a product; (h) a conduit for transferring product from the product suite to the filling suite; and (i) equipment in the filling suite for filling product.

In one embodiment, the transfer port apparatus implements a method of transferring a sterile liquid from a product suite to a filling suite by (a) sterilization of the means for transferring the sterile liquid to a product tube on a beta assembly; (b) insertion of an alpha assembly through a port in an isolation wall; (c) mating a beta assembly with the alpha assembly; (d) opening an alpha door into the filling suite; (f) connecting a means for transferring the sterile liquid from the product suite to the filling suite; and (g) transferring the sterile liquid from the product suite to the filling suite.

DESCRIPTION OF DRAWINGS

The following drawings present embodiments of the SLTP.

DESCRIPTION OF EMBODIMENTS

Overview

Figure 1:
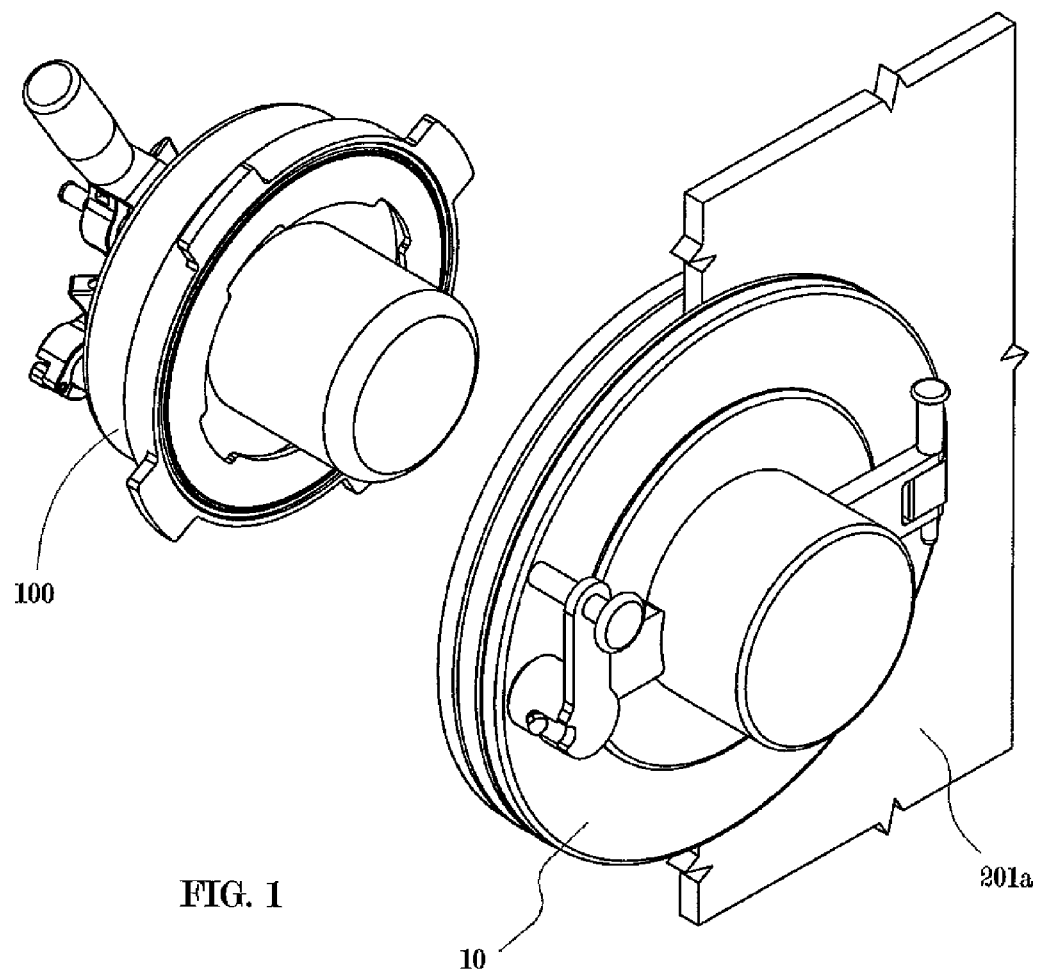
FIG. 1 is an isometric view of the alpha and beta assemblies of the sterile liquid transfer port.

The SLTP isolates the clean environment and provides uncontaminated transfer of the sterile liquid product. Isolation of the clean environment is accomplished by a single step sterilization process. Uncontaminated transfer of the sterile liquid product is accomplished by the combination of the alpha assembly and the beta assembly.

These key functions, including sterilization of the beta assembly 100, isolation of the alpha assembly 10, and docking of the beta assembly 100 to the alpha assembly 10, effectively isolate the dirty product suite 205 from the clean filling suite 204 (depicted in FIG. 5I) and enable the uncontaminated transfer of sterile liquid between the two suites 205 and 204. The process of uncontaminated transfer of sterile liquid is relatively easy to accomplish as it requires no special tools or technical skills. Multiple cleaning and sterilization steps are not required.

Detailed Description

The SLTP includes two main components—the alpha assembly 10 and the beta assembly 100.

Figure 5A:
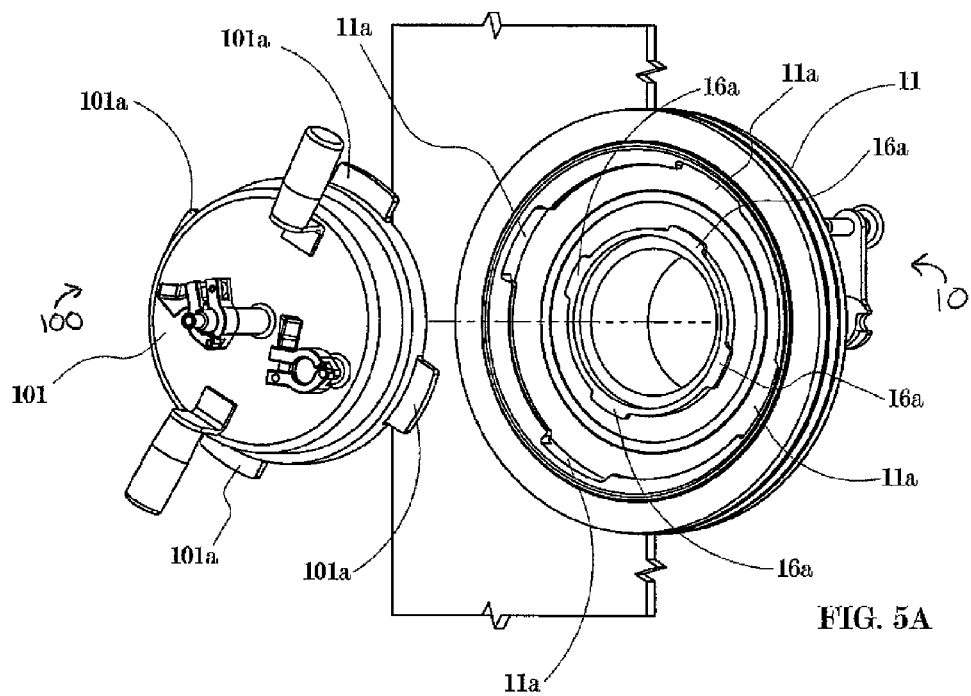
FIG. 5A is an isometric view of the beta assembly aligned for docking with the alpha assembly.
Figure 5B:
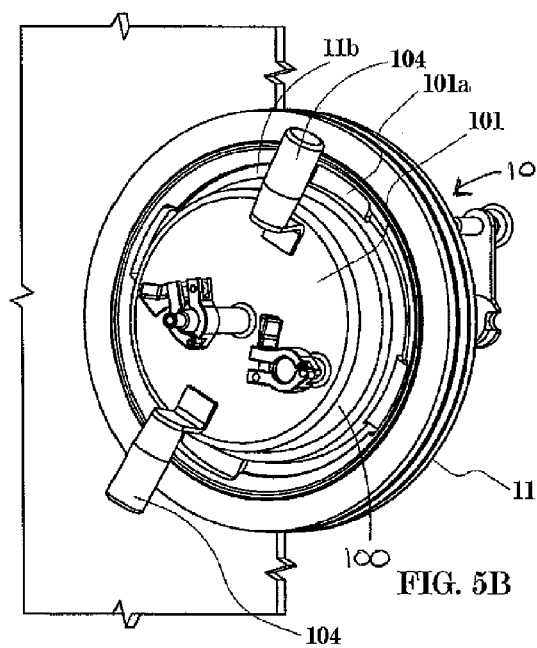
FIG. 5B is an isometric view of the beta assembly from the rear with the beta flange bayonets in the alpha bayonet receivers.
Figure 5C:
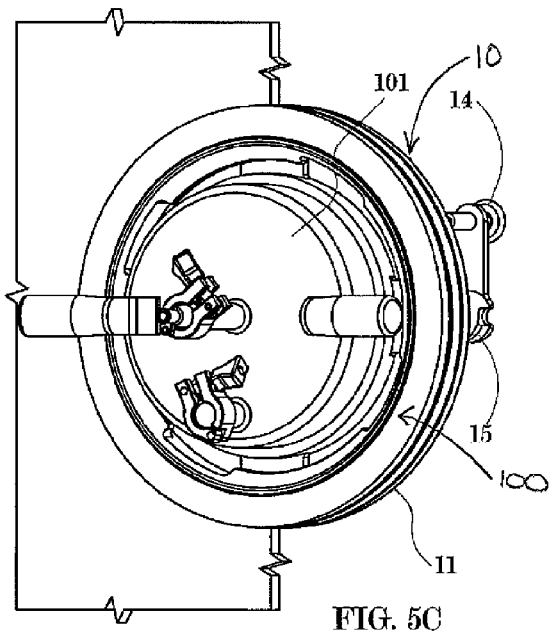
FIG. 5C is an isometric view of the fully docked beta assembly from the rear with the beta flange bayonets in the alpha bayonet receiver channels.
Figure 5D:
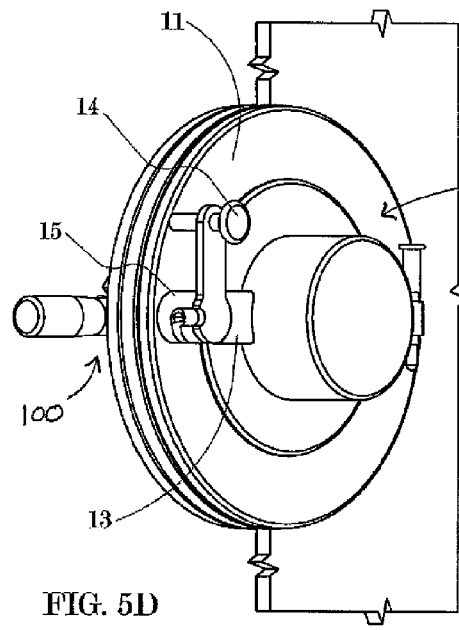
FIG. 5D is an isometric view of the alpha and beta assemblies from the front with the alpha door latched.
Figure 5E:
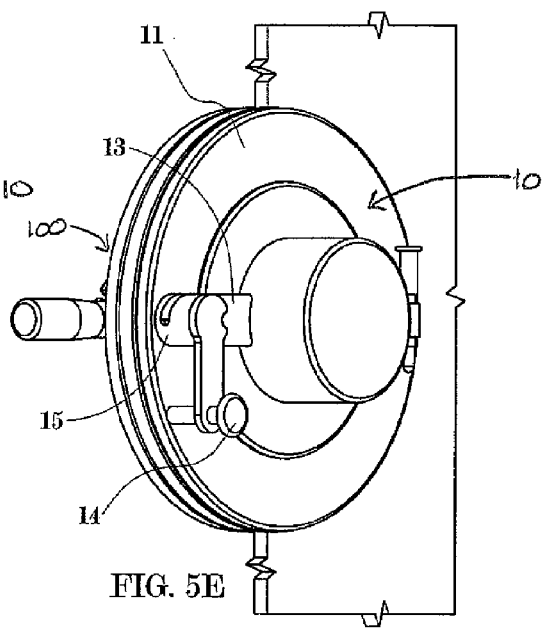
FIG. 5E is an isometric view of the alpha and beta assemblies from the front with the alpha door unlatched.
Figure 5F:
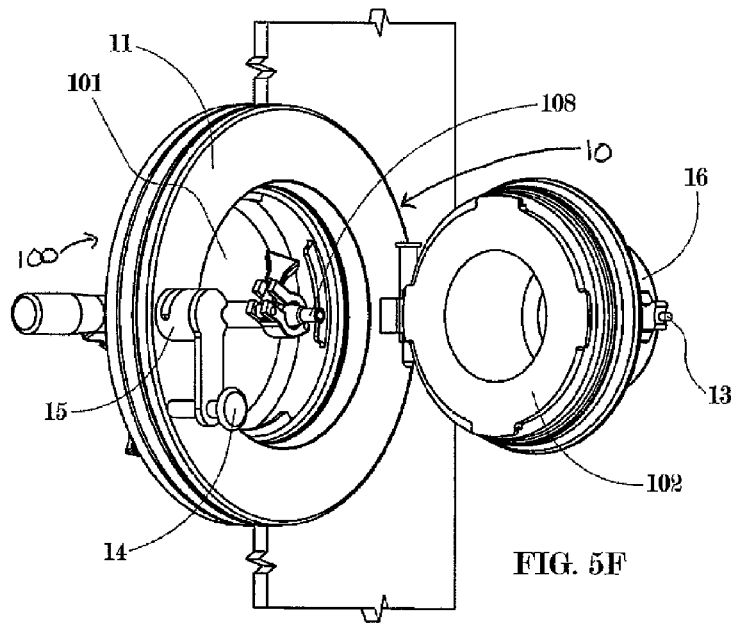
FIG. 5F is an isometric view of the alpha and beta assemblies from the front with the alpha door open.
Figure 5G:
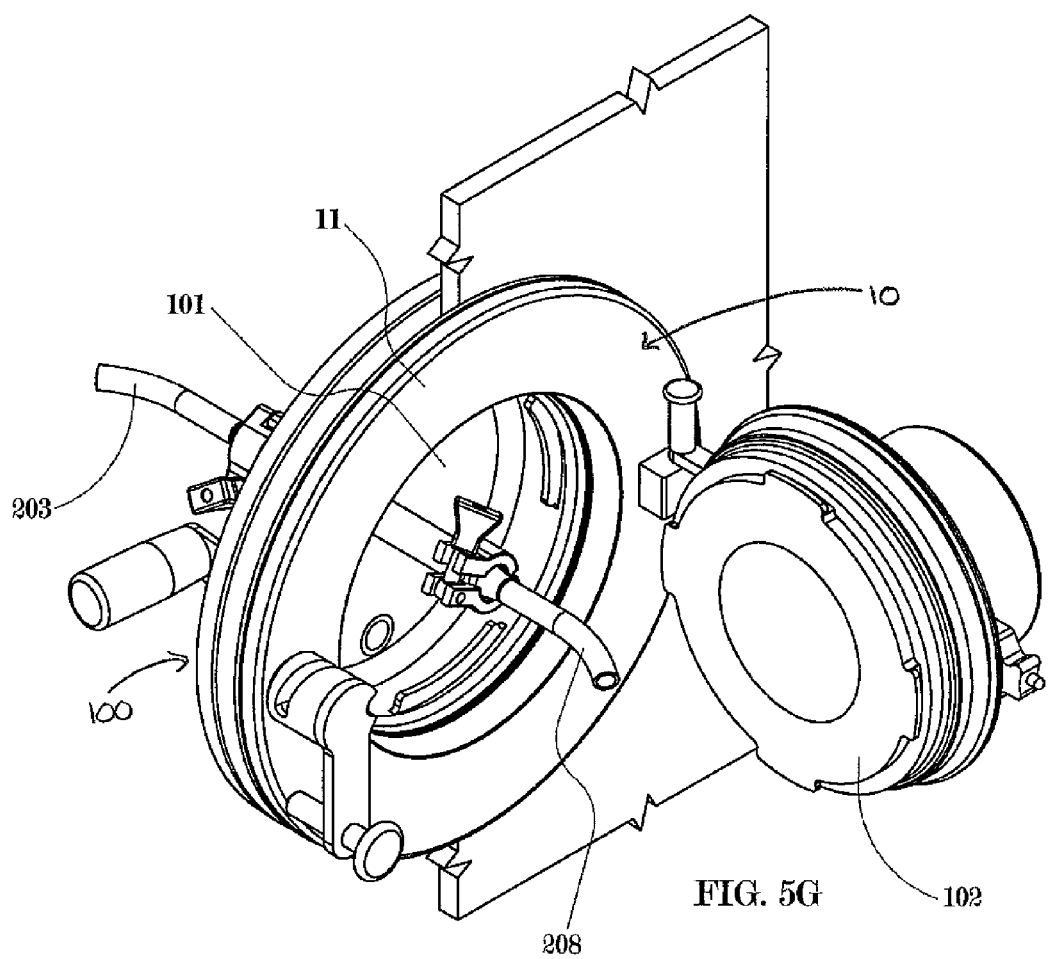
FIG. 5G is an isometric view of the alpha and beta assemblies of FIG. 5F with a product hose and a filling hose attached.
Figure 5H:
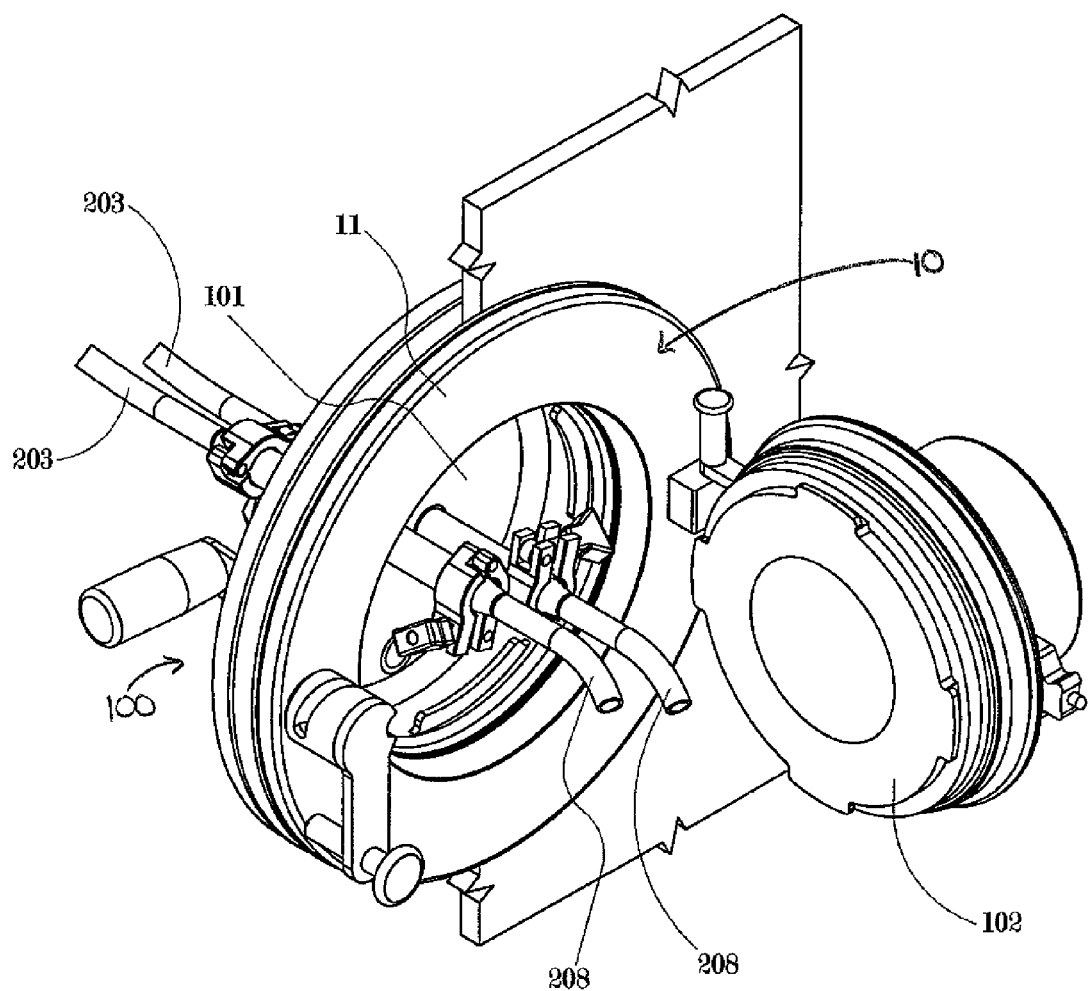
FIG. 5H is an isometric view of the alpha and beta assemblies of FIG. 5F with dual product hoses and filling hoses attached.
Figure 5I:
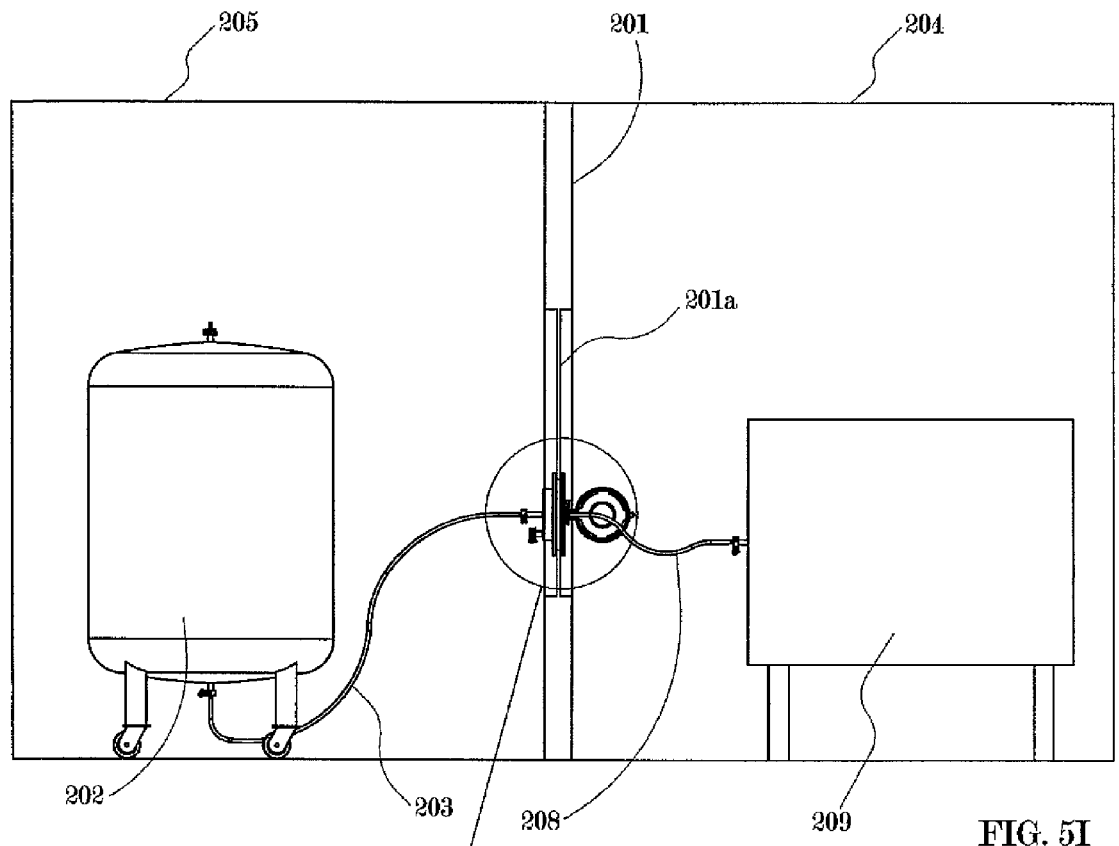
FIG. 5I is an elevation view of the sterile liquid transfer port in the filling mode.
Figure 5J:
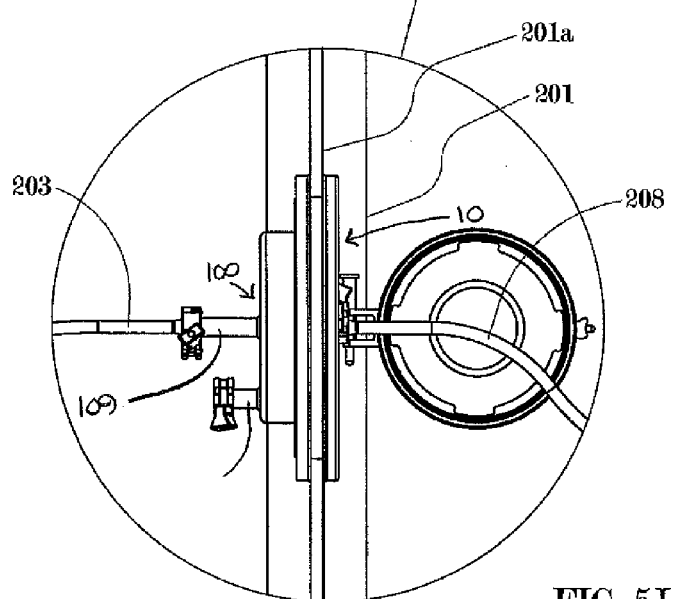
FIG. 5J is a detailed elevation view of FIG. 5H showing the sterile liquid transfer port in the filling mode.

FIG. 1 is an isometric view of the alpha and beta assemblies 10 and 100 of the sterile liquid transfer port, and can be understood in the context of FIGS. 5I and 5J. FIG. 5I is an elevation view of the SLTP in the filling mode, and FIG. 5J is a detailed view of the SLTP in the filling mode.

FIG. 5I depicts an SLTP system in a relevant environment, where an isolation wall 201 separates a first side 205 from a second side 204. The first side 205 can be a product suite having a product tank 202. The second side 204 can be a filling suite having filling equipment 209. The first side 205 can be a relatively "dirty" side, and can be classified as a Class 10,000 environment. The second side 204 can be a relatively "clean" side, which can be classified as a Class 100 environment. Often it can be desirable to transfer liquid from the product tank 202 on the "dirty" side to filling equipment 209 on the "clean" side without contamination of the liquid. An SLTP system can aid in such liquid transfer.

Figure 2A:
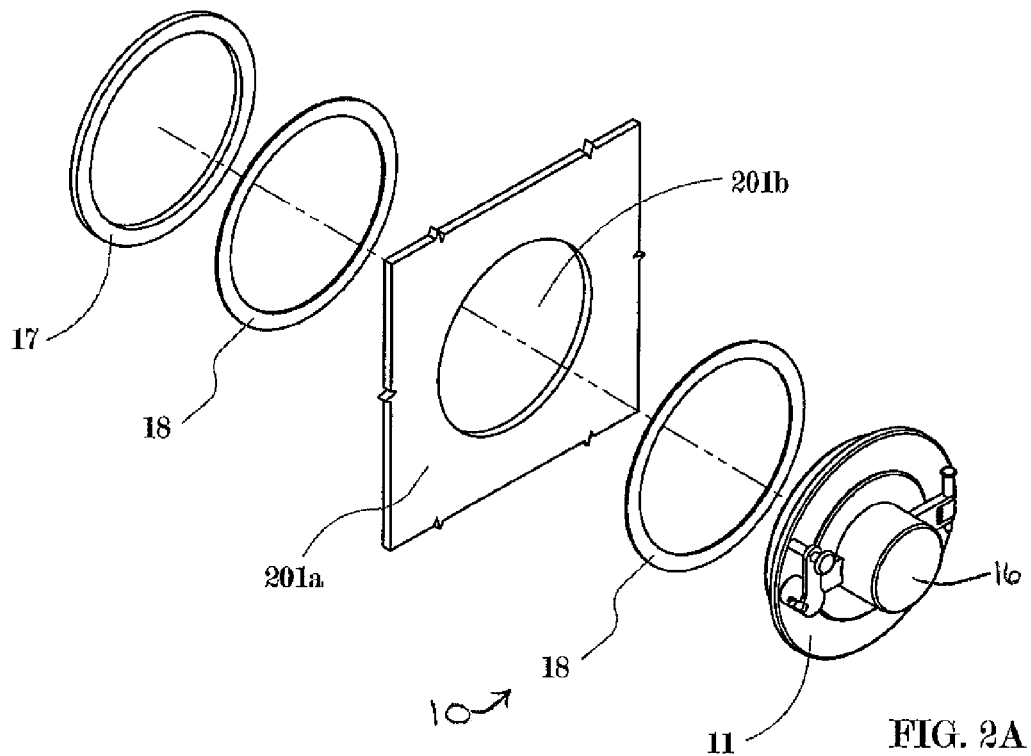
FIG. 2A is an exploded view of the alpha assembly.

As shown in FIGS. 1, 2A, and 5J, the alpha assembly 10 spans a transfer port 201b in an isolation window 201a. While the alpha assembly 10 can be primarily associated with the filling suite 204 (a Class 100 environment), as depicted in FIG. 5I, the alpha assembly 10 extends into the product suite 205, which is the relatively "dirty" environment such that its rear portion is exposed to the Class 10,000 environment. The beta assembly 100, however is exclusively associated with the product suite 205, or the "dirty" side, in various embodiments, and docks to that rear portion of the alpha assembly 10.

The alpha assembly 10 is configured to dock with the beta assembly 100, which is demonstrated progressively from FIG. 5A to FIG. 5F, and is described below. When the alpha 10 and beta assemblies 100 are docked, product can be transferred from the product suite 205 to the filling suite 204 (FIG. 5I) without breaking containment. In the filling mode, the beta assembly 100 is mounted in-line with the alpha assembly 10, as depicted in FIG. 5A. Turning to FIGS. 5F and 5G, when the alpha and beta assemblies 10 and 100 are docked together and the alpha door 16 is open, a rigid product tube 109 extends into the filling suite 204 and is ready for attachment to a sterile flexible filling hose 208. The sterile flexible filling hose 208 can deliver product (for example serum and vaccines) to commercially-sized containers for distribution.

FIG. 2A is an exploded view of the alpha assembly 10. The alpha assembly 10 has a first flange gasket 18, second flange gasket 18, a flange nut 17, an alpha flange 11 and an alpha door 16. The flange gasket 18 is a seal between the alpha flange 11 and the isolation window 201a. The seal prevents leakage from a first side of the isolation window 201a to a second side of the isolation window 201a, or the second side of the isolation window 201a to the first side of the isolation window 201a. A second flange gasket 18 is located on the opposite side of the isolation window 201a than that of the first flange gasket 18. The second flange gasket 18 also serves the purpose of preventing leakage from the product suite 205 side of the isolation window 201a into the filling suite 204 side of the isolation window 201a (depicted in FIG. 5I). Flange nut 17, located in the product suite side of the isolation window, secures the alpha flange 11 and the two flange gaskets 18 to the isolation window 201a. The alpha door 16 is disposed on the alpha flange 11.

Figure 2B:
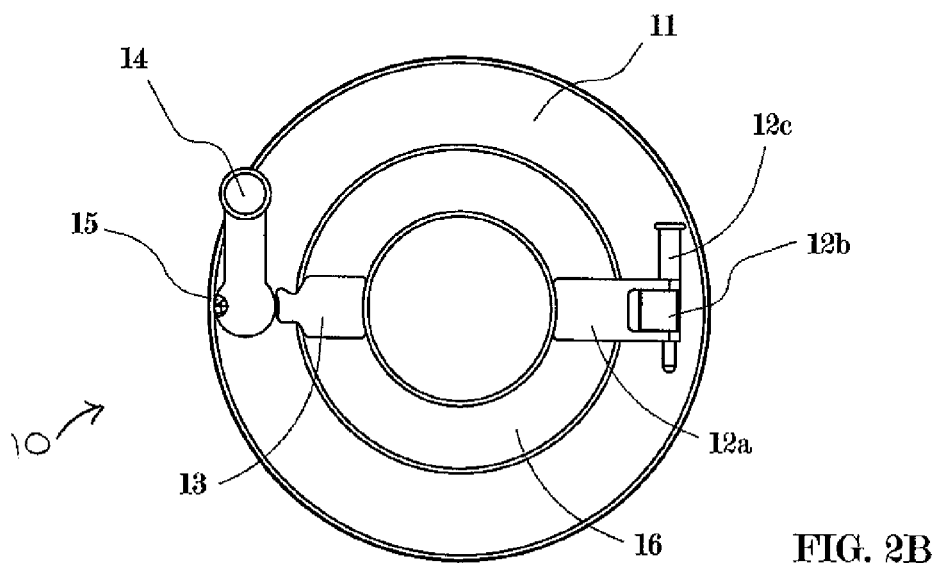
FIG. 2B is an elevation view of the alpha assembly.

FIG. 2B is an elevation view of the alpha assembly 10. The alpha assembly 10 comprises an alpha flange 11 and an alpha door 16. The alpha door 16 opens into one side of the isolation wall, which can be the filling suite side of the isolation wall depicted in FIG. 5I. In a variety of embodiments, the alpha door 16 is generally closed, unless a filling operation is in progress. As such, the alpha door 16 also remains closed during sterilization, which can include sterilization of the product tank 202, such as the one depicted in FIG. 5I. Sterilization generally takes place prior to initiation of a filling operation.

FIG. 2B also illustrates a latch 13 affixed to alpha door 16. A latch handle 14 engages with latch 13. When the latch handle 14 is in the up position, latch 13 is locked, as is the alpha door 16, in one example embodiment. The alpha door 16 is in a locked position whenever it is closed to avoid inadvertent contamination of clean side of the isolation wall, which can be the filling suite 204 from FIG. 5I, in one embodiment.

A mechanical latch interlock 15 can prevent improper or unwanted operation of the SLTP. For example, such improper operations could include: opening the alpha door 16 before the beta assembly 100 is docked with the alpha assembly 10; removing the beta assembly 100 from the alpha assembly 10 when the alpha door 16 is open; and rotating the latch handle 14 of the alpha door 16 when the alpha door 16 is open. Latch interlock 15 can prevent accidental opening of alpha door 16. The alpha door 16 can be opened when the beta assembly 100 is docked with the alpha assembly 10 due to automatic disengagement of the latch interlock 15 by the beta assembly 100. The alpha door 16 can then be safely opened by rotation of the latch handle 14, counter-clockwise 180°, in one embodiment, although other angles of rotation could be foreseen.

FIG. 2B also illustrates a hinge assembly 12 comprised of a hinge 12a, a hinge pivot block 12b, and a hinge pin 12c. The hinge 12a is affixed to alpha door 16. The hinge assembly 12 provides a pivot connection between the alpha door 16 and the alpha flange 11 in a plane. Hinge 12a allows pivoting or rotation of the alpha door 16 around the hinge pin 12c to both open and close the alpha door 16. The hinge pivot block 12b acts as a support guide to maintain the alpha door 16 in horizontal alignment during rotation or pivoting and during the time it is in the open position.

Figure 2C:
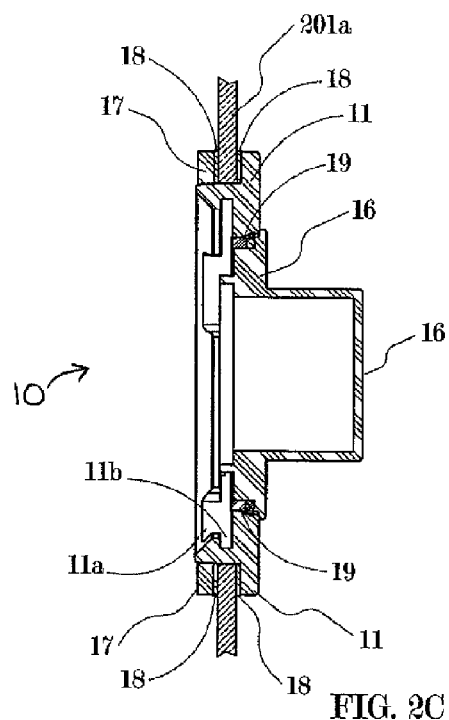
FIG. 2C is a cross-sectional view of the alpha assembly of FIG. 2B.

FIG. 2C is a cross-sectional view of the alpha assembly 10 of FIG. 2B. The alpha assembly 10 is intended to maintain isolation of a first side of an isolation wall from a second side of an isolation wall, such as the product suite 205 from the filling suite 204 as depicted in FIG. 5I. Such isolation is maintained regardless of whether the SLTP is in a sterilization mode or a filling mode. The installation of the alpha flange 11 is relatively permanent, while the beta flange 101 is often inserted and removed. Now an example structure of the alpha assembly 10 will be described.

The alpha assembly 10 is comprised of a flange 11, alpha door 16, bayonet receiver 11a, bayonet receiver channel 11b, flange nut 17, alpha seal 19, gasket 18 on the product suite side, and gasket 18 on the filling suite side. The alpha seal 19 surrounds the inside of the alpha door 16 and seals the door 16 to the flange 11 upon closure.

Typically, an isolation window 201a is installed in an opening in the isolation wall 201 and the alpha flange 11a is installed in the transfer port 201b in the isolation wall 201. The alpha flange 11 is inserted into a transfer port 201b (see FIG. 2A) in an isolation wall 201. Prior to insertion of flange 11, gasket 18 on the filling suite side is put in place around the flange 11. The isolation window 201a is used to monitor activity in the product and/or filling suites 204 and 205. After the alpha flange 11 is installed into a transfer port 201b, gasket 18 on the product suite 204 side is placed around the flange 11 and flange nut 17 is tightened down against the isolation window 201a or the isolation wall 201, as the case may be.

Figure 2D:
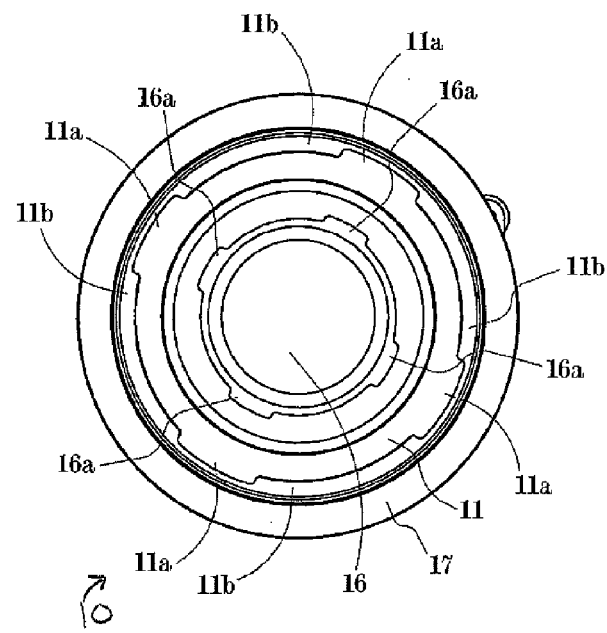
FIG. 2D is an elevational view of the alpha assembly viewed from the rear.

FIG. 2D is an elevational view of the alpha assembly 10 viewed from the rear. Alpha bayonet receiver 11a can also be referred to as a third connector set 11a, and is configured for mating engagement with a beta flange bayonet 101a when a beta assembly 100 is docked with the alpha assembly 10. As will be explained in more detail, below, the beta flange bayonet 101a can be referred to as a first connector set. After initial docking, handles 104a (see FIG. 3C) are used to rotate the beta flange bayonets 101a counter-clockwise to releasably lock the beta flange bayonets 101a under the alpha bayonet receiver channel 11b. Alpha door bayonets 16a, which can be referred to as a fourth connector set 16a, are also configured for mating engagement with beta cover bayonet receivers 102b, where the beta cover bayonet receivers 102b can be referred to as a second connector set 102b. Handles 104a are used to further rotate the docked beta assembly 100 counter-clockwise to rotation of the beta flange releasably lock the alpha door bayonets 16a under the beta cover bayonet receiver channels 102c.

Figure 2E:
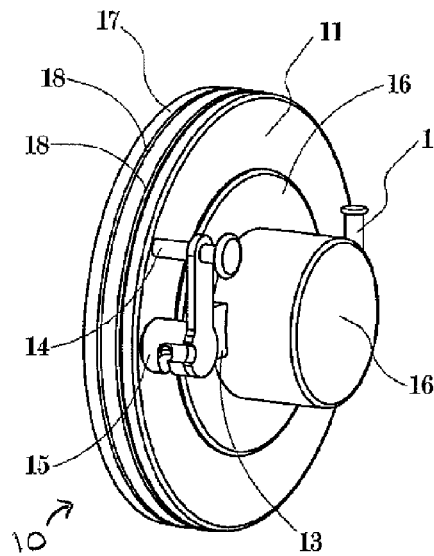
FIG. 2E is an isometric view of the alpha assembly with the alpha door closed.

FIG. 2E is an isometric view of the alpha assembly 10 with the alpha door 16 closed. As previously mentioned, latch handle 14 is engaged with latch 13. When latch handle 14 is in the up position it locks latch 13 and thereby alpha door 16.

Figure 2F:
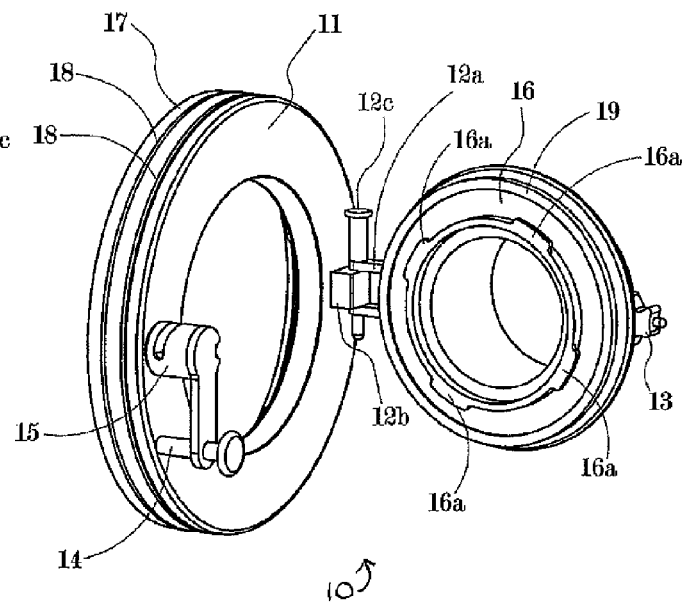
FIG. 2F is an isometric view of the alpha assembly with the alpha door open.

FIG. 2F is an isometric view of the alpha assembly with the alpha door open. To open the alpha door 16, latch handle 14 is rotated counter-clockwise 180°.

Figure 3A:
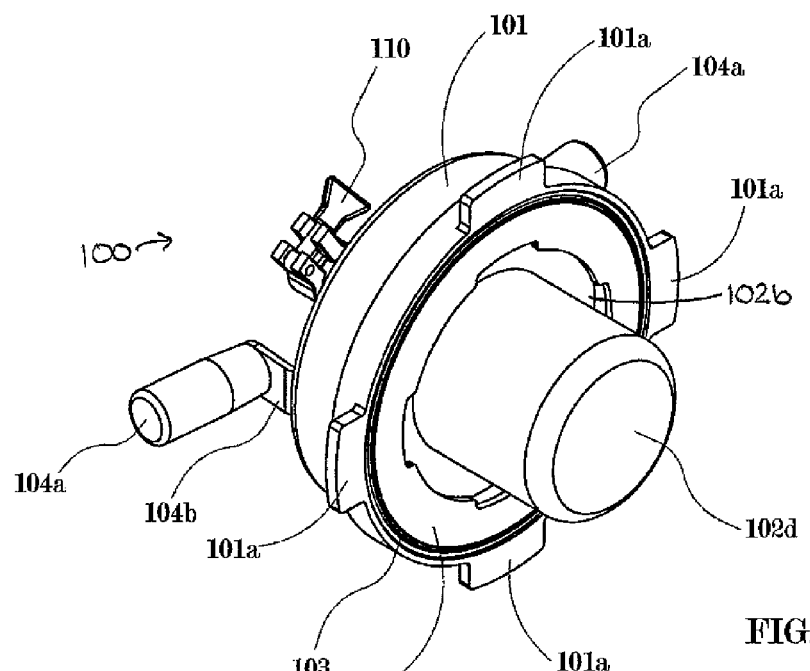
FIG. 3A is an isometric view of the beta assembly from the front.

FIG. 3A is an isometric view of a beta assembly 100 from the front. The beta assembly is configured for connection with the alpha assembly from the first side of the isolation wall for sterile transfer of a product. The beta assembly generally has a housing having a first side 101 and second side 102 that define an interior space, where the first side 101 can be a beta flange 101 and the second side 102 can be a beta cover 102. A first connector set 101a is defined on the first side 101 and a second connector set 102b is defined on the second side 102. The beta flange 101 can be releasably locked to the beta cover 102. In at least one embodiment, flange bayonets 101a on the first side 101 of the housing are configured to engage bayonet receivers 111b of the docking cover. The beta assembly 100 also has a beta seal 103.

Figure 3B:
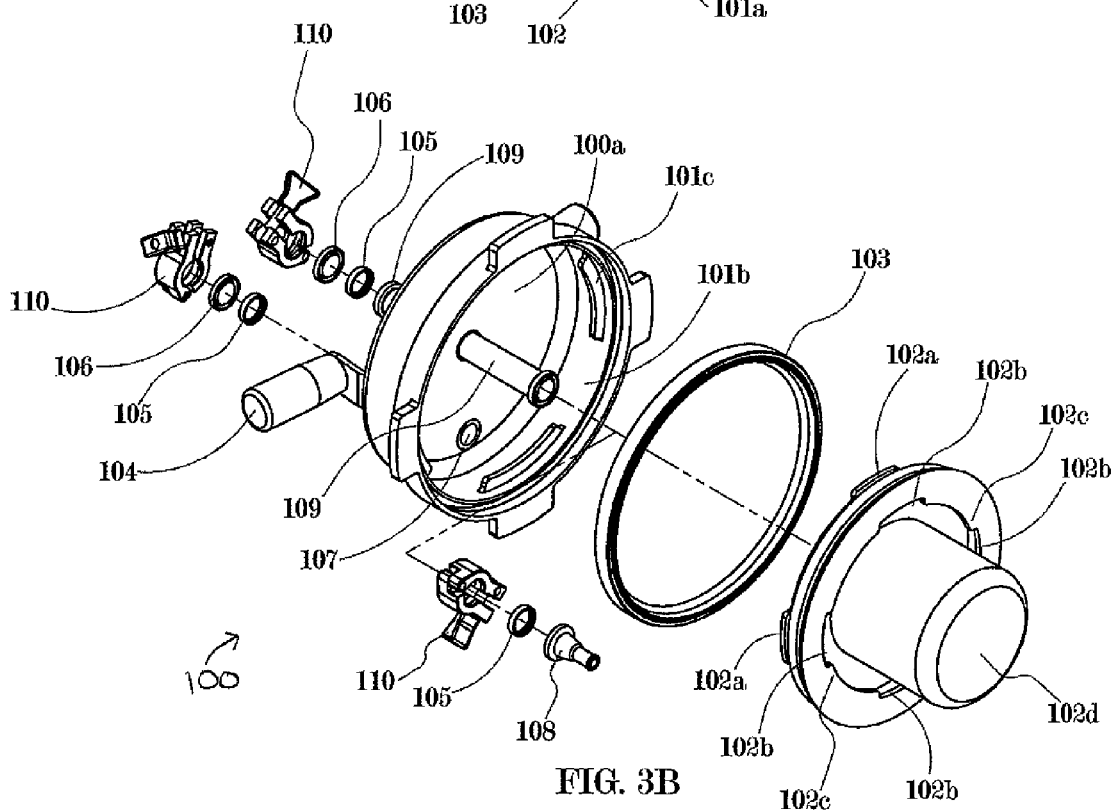
FIG. 3B is an exploded, isometric view of the beta assembly from the front.

The beta cover 102, includes a beta cover end cap 102d that provides a closed interior space 100a for the rigid product tube 109 and a rigid drain tube 107 (shown in FIG. 3B). The product tube 109 defines a passage from the interior space 100a to outside of the housing. The closed interior space 100a created by the cover end cap 102d is used in the sterilization mode. Sanitary fitting clamp 110 connects a flexible product hose 203 to a rigid product tube 109 for use during the sterilization process and for transfer of product during the filling process. The beta cover 102 is releasably locked to the beta flange by alignment of the beta cover bayonets 102a with the bayonet cover receivers 101b of the beta flange 100, followed by rotation of the beta cover bayonets 102a under the beta cover bayonet receiver channels 101c.

Beta flange 101 comprises at least one handle, in some embodiments two handles, and brackets 104a and 104b, sanitary fitting clamp 110, and flange bayonets 101a. A first connector set 101a, which can be flange bayonets 101a, are aligned with the alpha bayonet receiver 11a during docking of the beta assembly 100 with the alpha assembly 10. Cover seal 103 seals the beta cover end cap 102 to the beta flange 101 when the beta cover 102 is connected to beta flange 101. Handles 104a are used to rotate the beta flange bayonets 101a counter-clockwise to releasably lock the beta flange bayonets 101a under the alpha bayonet receiver channels 11b. Alpha door bayonets 16a are configured for mating engagement with beta cover bayonet receivers 102b. Rotation of the beta flange bayonets 101a counter-clockwise also releasably locks the alpha door bayonets 16a under the beta flange bayonet receiver channels 102c.

FIG. 3B is an exploded, isometric view of the beta assembly 100 from the front. In this view, the interior space 100a of the beta flange can be clearly seen. A first hose connection device incorporating a combination of the sanitary fitting clamp 110, the sanitary fitting cap 106, and the sanitary fitting seal 105 provides the connection between a flexible product hose 203 from the product tank 202 and the rigid product tube 109 without the use of tools. A second hose connection device incorporates a combination of the sanitary fitting clamp 110, sanitary fitting seal 105, and sanitary fitting cap 106, to provide a connection between a product tube 109 and a flexible filling hose 208 without the use of tools. A rigid drain tube 107 is shown in the interior space 100a and is combined with the sanitary fitting clamp 110, sanitary fitting seal 105, and sanitary fitting adaptor 108. It provides the connection between the interior space 100a of the beta assembly 100, the rigid drain tube 107, and the flexible steam drain hose 207. The rigid drain tube 107 is used during the sterilization process. The rigid drain tube 107 defines a passage from the interior space 100a to outside of the housing of the beta assembly 100.

Figure 3C:
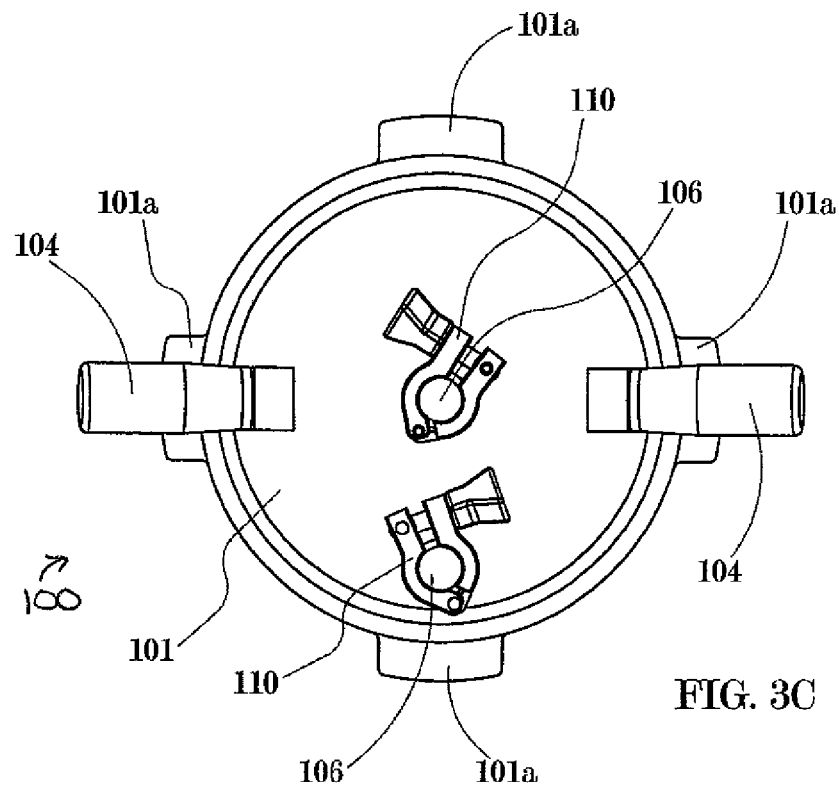
FIG. 3C is an elevational view of the beta assembly from the rear.
Figure 3D:
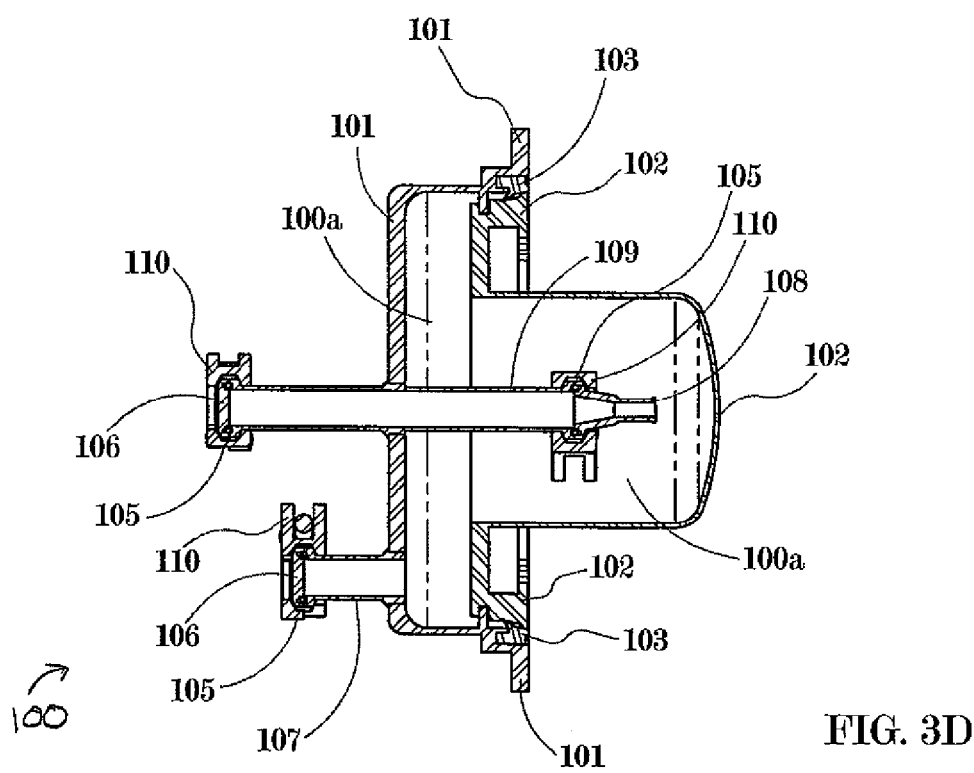
FIG. 3D is a cross-sectional view of the beta assembly of FIG. 3A.

FIG. 3C is an elevational view of the beta assembly from the rear. FIG. 3D is a cross-sectional view of the beta assembly 100 of FIG. 3A. FIG. 3D is a cross-sectional view of the beta assembly 100 of FIG. 3A. The product port and the drain port, as shown at the rear of FIG. 3D, are capped with sanitary fitting adaptors 106 for storage of the beta assembly.

Figure 4A:
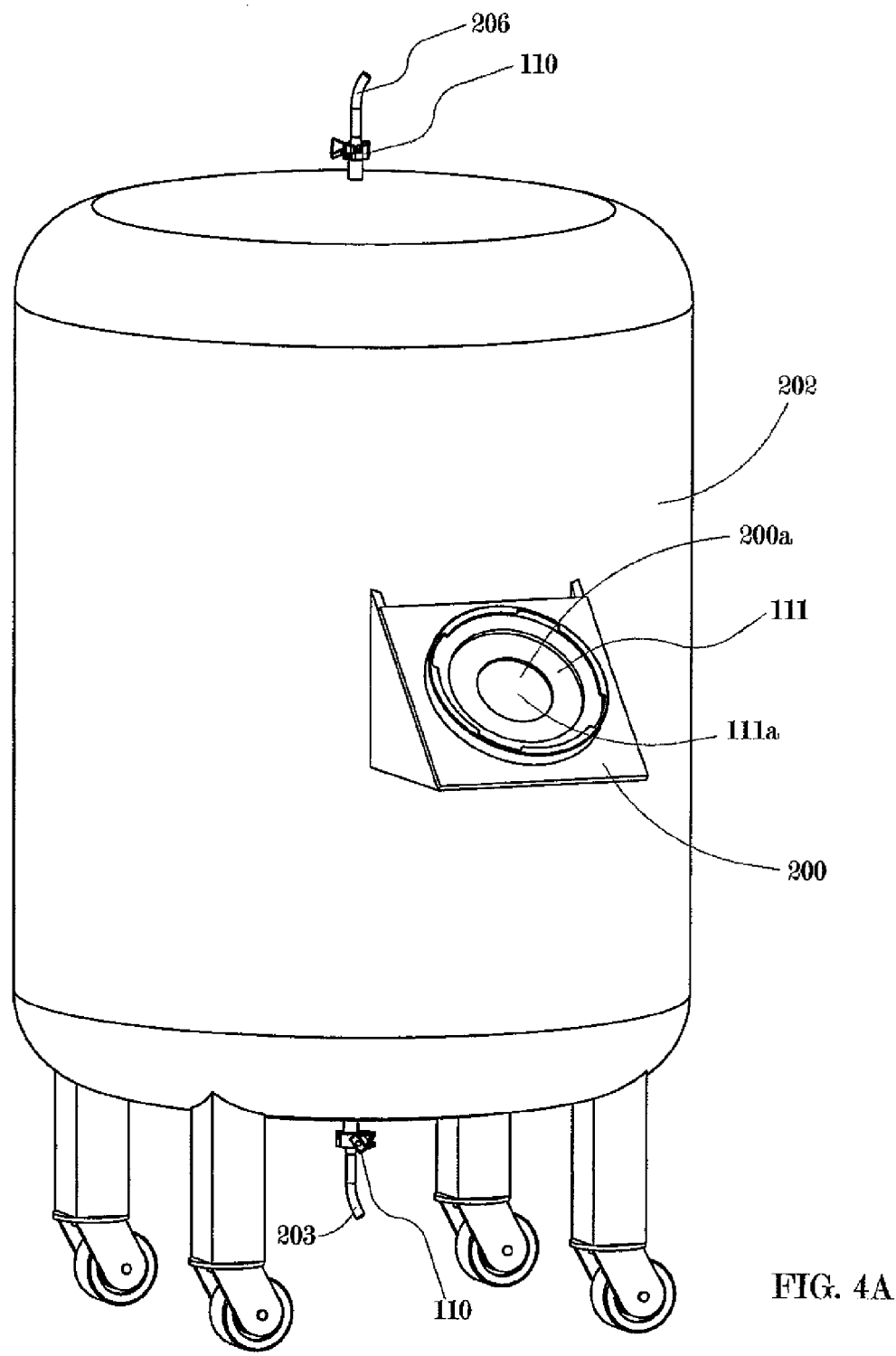
FIG. 4A is an isometric view of the product tank with the docking cover located on the product tank.

A docking cover is generally located on a first side of an isolation wall and is configured for connection with a beta assembly during a sterilization process. FIG. 4A is an isometric view of the product tank 202 with the docking cover 111 located on the product tank. The docking cover 111 may be located on a wall, bench, or other convenient place within the product suite 205. The tank 202 is shown with wheels to indicate that the tank 202 is movable within the product suite 205 or movable to an entirely different product suit. It is typical that the SLTP will include multiple product tanks 202 and beta assemblies 100, yet only one alpha assembly 10. The beta assemblies 100 can also be located in a mobile product suite 205. The flexible product hose 203 is used as steam supply hose during sterilization and for transferring product to the beta assembly during filling. Each hose 203, 207, and 208 attaches to a sanitary fitting adaptor 108 when connected to the beta assembly 100.

Figure 4B:
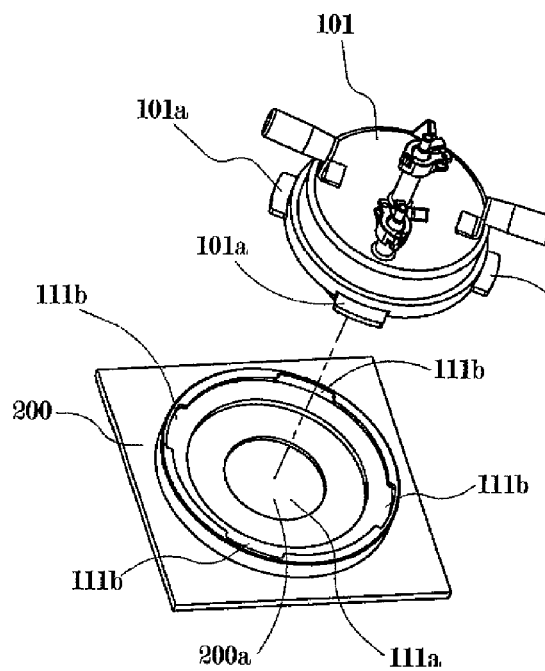
FIG. 4B is an isometric view of the beta assembly aligned for docking with the docking cover.

FIG. 4B is an isometric view of the beta assembly 100 aligned for docking with the docking cover 111. The docking cover 111 generally defines an opening to accommodate a portion of the housing 100. The docking cover 111 is attached to a mounting plate 200 that in turn is attached to the outside of the product tank 202. The beta assembly 100, beta cover 102, and the mounting plate 200 are not connected in any way to the inside of the tank 202. The docking cover 111 has bayonet receivers 111b, which can be referred to as a fifth connector set 111b, for engagement with the first connector set 101a, or beta flange bayonets 101a, on the beta assembly 100 As will be understood by those of skill in the art, the first connector set 101a and fifth connector set 111b can be a variety of mateable components that mate in a variety of different ways even though the connector sets described in the implementations disclosed herein are generally bayonet connections. In at least one embodiment, the beta assembly 100 mounts to the docking cover without using any tools.

Figure 4C:
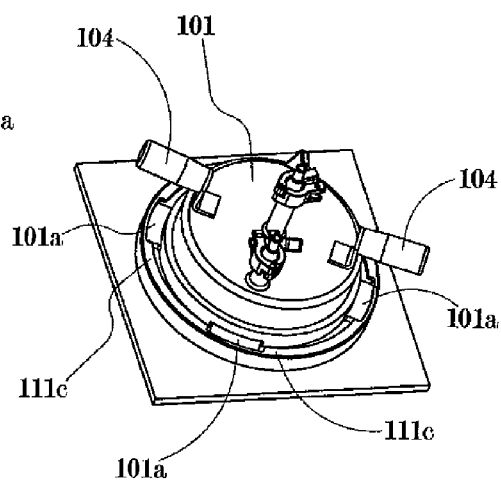
FIG. 4C is an isometric view of the beta assembly with the beta flange bayonets in the docking cover bayonet receivers.

As shown in FIG. 4C, the beta cover end cap 102d is inserted into the docking cover opening 111a, which is in alignment with the mounting plate opening 200a.

Figure 4D:
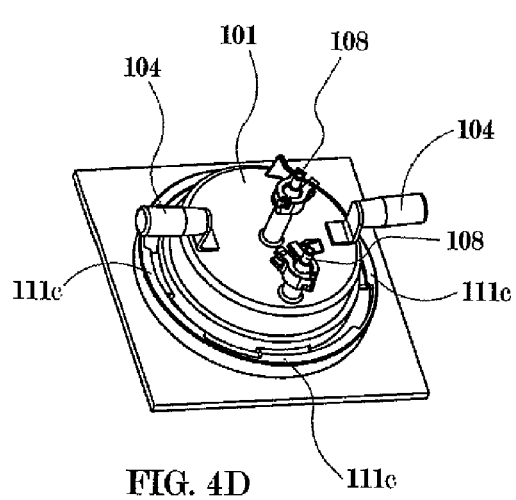
FIG. 4D is an isometric view of the beta assembly fully docked with the beta flange bayonets in the docking cover bayonet receiver channels.

After insertion of the bayonets 101a into the bayonet receivers 111b, the beta assembly, as shown in FIG. 4D, is mounted to the docking cover by rotating the beta assembly counter-clockwise, using handle assemblies 104, thereby rotating the beta flange bayonets 101a in the docking cover bayonet receiver channels 111c. Sanitary fitting adaptors 108 are also shown.

Figure 4E:
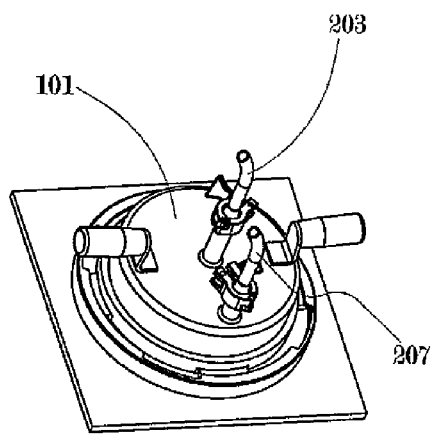
FIG. 4E is an isometric view of the docked beta assembly with a product hose and a steam drain hose attached.

FIG. 4E is an isometric view of the beta assembly with a flexible product hose 203 and a steam drain hose 207. The product hose 203 is connected to the product tube 109 of the beta assembly 100. Likewise, the drain hose 207 is connected to the drain tube 107.

Figure 4F:
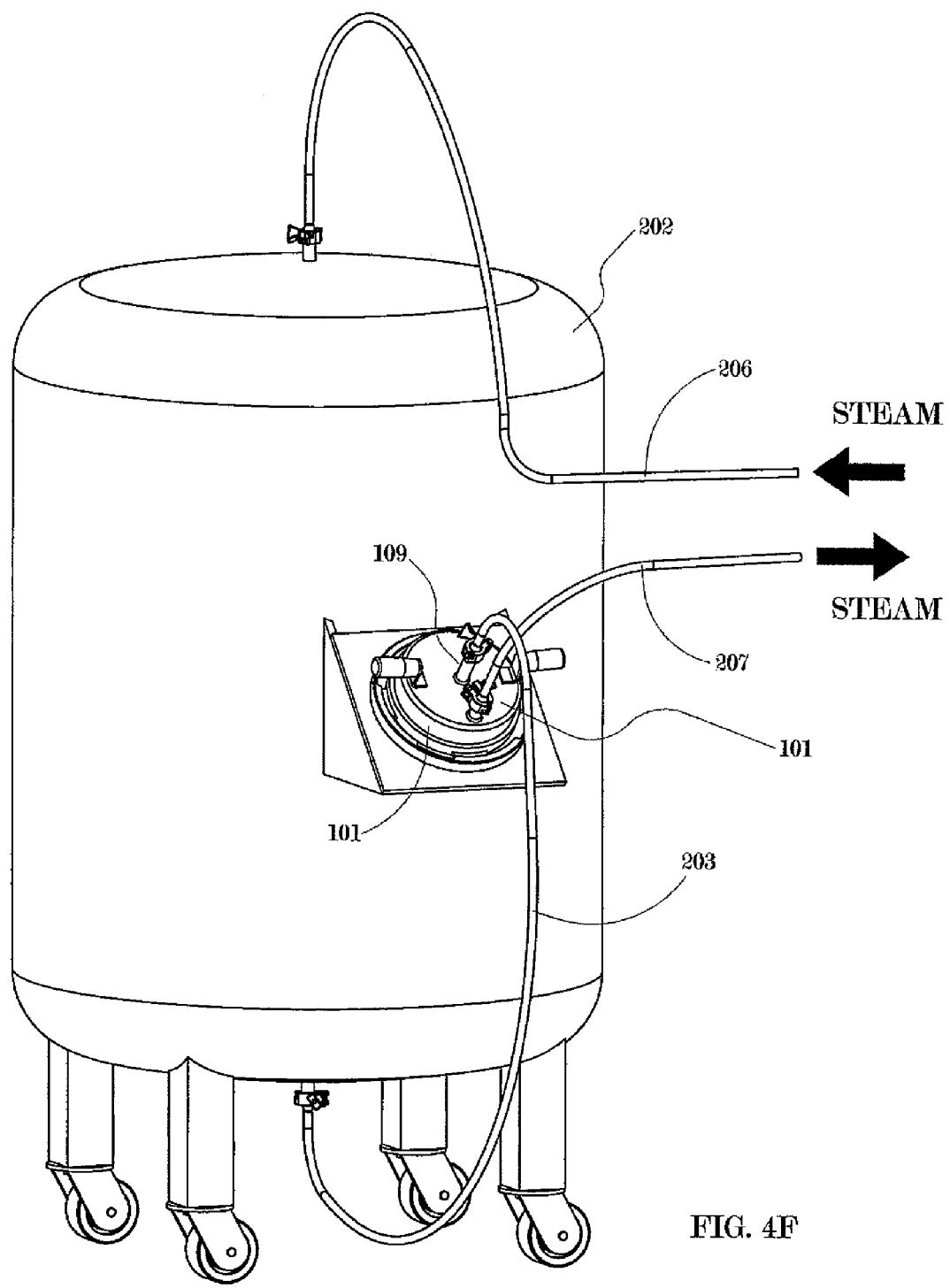
FIG. 4F is an isometric view of the product tank in the steam sterilization mode.
Figure 4G:
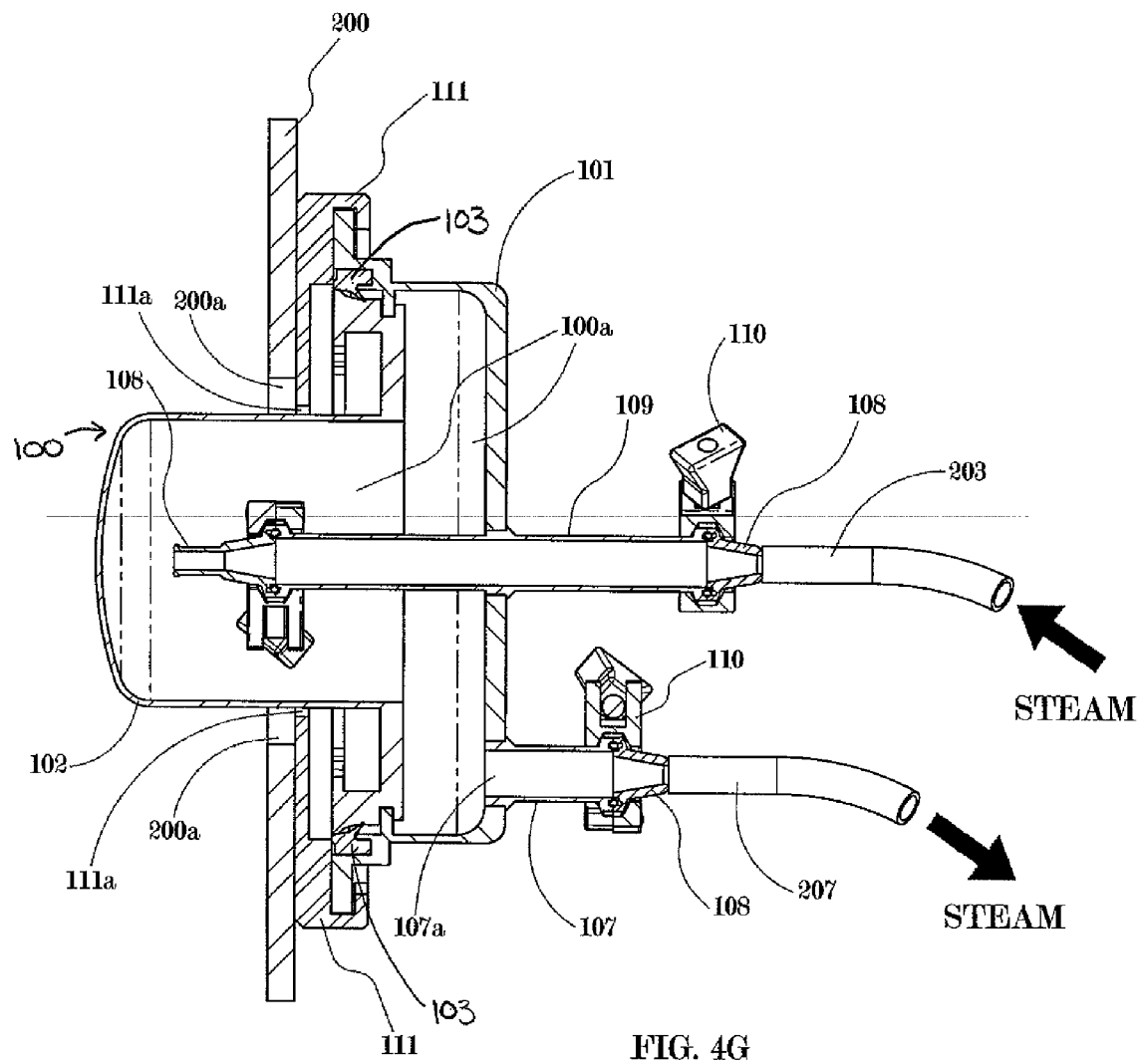
FIG. 4G is a cross-sectional view of the beta assembly of FIG. 4F in the steam sterilization mode.

FIGS. 4F and 4G are isometric views of the product tank 202 and the beta assembly 100 docked with the docking cover 111 in the steam sterilization mode. Steam from a steam source is introduced into the top of the product tank 202 and passes through the flexible steam supply hose 206. Steam exits at the bottom of the tank 202 through the flexible product hose 203 and into the beta assembly 100 via rigid product tube 109. Steam continues its travel through the interior 100a of the beta assembly 100, out the rigid drain tube 107, through the flexible steam drain hose 207, and into a condensate tank for disposal (not depicted).

FIG. 4G illustrates the detail of the beta assembly interior 100a and the hose connections to the beta assembly 100. As is viewable from the Figure, a seal 103 positioned between a portion of the beta cover and a portion of the beta flange, wherein the docking cover contacts the seal when the beta assembly is mated to the docking cover. By contacting the seal, the docking cover supports the seal during the sterilization process. The combination of the beta cover, beta flange and docking cover contact the seal on all sides of the seal. Without the cover, steam pressure during the sterilization process could cause the seal to be forced out of its seat, thereby possibly causing a leak which would be a failure of the sterilization process. With the docking cover, the seal 103 is further supported and a successful sterilization process is more likely.

The beta assembly 100 is an integral part of the sterilization process. The sterilization system comprises the interior surfaces of the empty (i) product tank 202, (ii) flexible product hose 203, (iii) flexible steam supply hose 206, (iv) flexible steam drain hose 207, (v) beta assembly 100, and (vi) steam source. The beta assembly 100 comprises the beta assembly interior 100a. The interior 100a, comprises the (i) rigid product tube 109, (ii) beta flange 101, (iii) beta cover 102, and (iv) outlet 107a of the rigid drain tube.

Exposure to elevated temperature and pressure for an extended period ensures sterilization of all of the internal surfaces of the sterilization system. The alpha door 16 of the alpha assembly 10 is closed and sealed while sterilization takes place. Saturated steam at the elevated temperature and pressure is circulated through the sterilization system. The saturated steam is injected through the system at a working pressure of about 36.3 psi (depending upon the product type). The saturated steam temperature is about 150° Centigrade (depending upon the product type) when it enters the system. The required level of sterilization is maintained by continually monitoring the steam temperature at the rigid drain tube 107 to ensure that the steam temperature at the drain tube 107 remains at or about 150° Centigrade (depending upon the product type). After the system is sterilized, condensate is removed from the system by injecting hot, dry air through the system.

Upon completion of the sterilization process the beta assembly 100 is undocked from the docking cover 111 and docked with the alpha assembly 10. During the sterilization process the flexible product hose 203 was connected at the rear of the beta assembly 100 to the rigid product tube 109. To maintain sterilization, the flexible product hose 203 must remain connected. The flexible steam drain hose 207 and the sanitary fitting adaptor 108 must be removed from the rigid drain tube 107 and replaced with the sanitary fitting cap 106.

FIG. 5A is an isometric view of the beta and alpha assemblies 100 and 10 with the beta assembly aligned for docking with the alpha assembly. A first connector set 101a on the first side 100 and a second connector set 102b on the second side 102 (visible in FIG. 3A, for example), where the first connector set 101a is configured to be mated with a third connector 11a set on the alpha assembly 10 and the second connector set 102b is configured to be mated with a fourth connector set 16a on the alpha assembly 10. The first connector set 101a can also be configured to be mated with a fifth connector set on a product tank as described above in the discussion of FIG. 4B-4E. In a variety of embodiments, including the one depicted and described herein, the first, second, third, fourth and fifth (described in the discussion of FIG. 4A), are bayonet connections. FIG. 5B is an isometric view of the beta assembly with the beta flange bayonets 101a received in the alpha bayonet receivers 11a. Those skilled in the art will appreciate that a variety of other types of connections can be employed and still remain in the scope of the technology disclosed herein.

As shown in FIG. 5C, the beta flange bayonets 101a are then rotated counter-clockwise under the alpha bayonet receiver channels 11b. The first 101a and third 11b connector sets can be configured to engage and disengage upon rotation with respect to each other. Likewise, the second and fourth connector sets can be configured to engage and disengage upon rotation with respect to each other, although other means of engaging and disengaging the first and third connector sets can be employed.

FIG. 5D is an isometric view of the alpha and beta assemblies 10 and 100 with the alpha door 16 latched.

FIG. 5E is an isometric view of the alpha and beta assemblies 10 and 100 with the alpha door 16 unlatched.

FIG. 5F is an isometric view of the alpha and beta assemblies with the alpha door 16 open, thereby allowing access to the sanitary fitting adaptor 108 for attachment to the flexible filling hose 208.

FIG. 5G is an isometric view of alpha and beta assemblies 10 and 100 having one rigid product tube 109. FIG. 5H is an isometric view of the alpha and beta assemblies 10 and 100 having two rigid product tubes 109. In certain cases, two substances may be differentially metered from separate product tanks into the respective product tubes 109 for combination into a two-part medicant. In this manner any number of individual product tubes may be employed to mix the various substances together. In FIGS. 5G and 5H, the rear of the beta cover 102 is captured by the alpha door 16 when the beta assembly 100 is engaged with the alpha assembly 10. The flexible filling hose 208 extends into the filling suite 204.

FIG. 5I is an elevation view of the SLTP in the filling mode.

FIG. 5J is a detailed view of the SLTP in the filling mode. Transfer of product to the filling suite 204 may be accomplished by pumping, gravity feed, or pressurization of the product tank 202. Typically, product is stored under pressure.

As shown by FIGS. 5A-5J, the alpha assembly 10 and the beta assembly 100 implement the process of uncontaminated transfer of sterile liquid product. The product suite 205 is always isolated from the filling suite 204 by an alpha assembly 10. The alpha assembly 10 has an interface for docking the beta assembly 100. The alpha assembly 10 is configured so the alpha door 16 cannot be opened without the beta assembly 100 docked to the alpha assembly 10. This ensures that the product suite 205 will not contaminate the filling suite 204.

To transfer sterile liquid product from the product tank 202 to the filling suit 204, (i) the flexible steam supply hose 206 is shut-off from the product tank 202, (ii) the flexible steam drain hose 207 is shut-off from the sanitary fitting adaptor 108 on the beta assembly 100, the adaptor is removed from the beta assembly, and the adaptor 108 is replaced with a plug; and (iii) the beta assembly 100, with its attached flexible product hose 203, is undocked from the docking cover 111 and docked with the alpha assembly 10. And the product tank 202 is filled with product.

Rotating the beta assembly 100 and docking it to the alpha assembly 10 causes four events to simultaneously occur. First, during docking the beta flange 101 becomes rigidly attached to the alpha flange 11. Second, docking causes the beta cover 102 to become detached from the beta flange. Third, the beta cover 102 whose external surfaces have been exposed to the product suite 205 becomes attached to the alpha door 16. All external surfaces are sealed inside the alpha door 16 by the alpha seal 19. Finally, the docking process disengages the interlock mechanism on the alpha assembly 10 thus enabling the alpha door 16 to be safely opened. Once opened, the beta cover 102 becomes separated from the beta flange 101 thereby exposing the sterile rigid product tube 109, sterile sanitary fitting seal 105, sterile sanitary fitting adaptor 108, and sterile sanitary fitting clamp 110 to the clean filling suite 204. Attachment of a flexible filling hose 208 enables transfer of the sterile liquid without contamination from the product suite 205 into the filling suite 204 and subsequently into the filling equipment 209.

What is claimed is:

1. An assembly for a sterile liquid transfer port system comprising:
    a beta cover;
    a beta flange releasably locked to the beta cover providing interior space;
    a product tube defining a passage from the interior space configured for use during the sterilization process and further configured for transfer of product during a filling process;
    a drain tube defining a passage from the interior space to be used during a sterilization process;
    wherein the beta flange has flange bayonets configured to be aligned with an alpha assembly;
    cover bayonet receivers of the beta cover configured for mating engagement with alpha door bayonets of the alpha assembly;
    a docking cover, wherein the flange bayonets are further configured to be mated with the docking cover.

2. The assembly of claim 1, further comprising handles to rotate the flange bayonets.

3. The assembly of claim 1, wherein the docking cover is located at one of the group consisting of: a wall, a bench, and a product tank.

4. The assembly of claim 1, wherein docking the beta assembly to the alpha assembly causes the beta cover to become detached from the beta flange.

5. The assembly of claim 1 configured such that steam exits a tank into the product tube, through the interior space, and out the drain tube in a sterilization mode.

6. The assembly of claim 1, further comprising two or more product tubes.

7. The assembly of claim 1, further comprising a fitting seal providing connection between a product hose and the product tube.

* * * * *